(12) United States Patent
Weist

(10) Patent No.: US 8,529,507 B2
(45) Date of Patent: Sep. 10, 2013

(54) CANNULA PROTECTOR AND SINGLE-USE SYRINGE SYSTEM

(75) Inventor: Mario Weist, Waidhofen (AT)

(73) Assignee: Husky Injection Molding Systems Ltd., Bolton Ontario (CA)

( * ) Notice: Subject to any disclaimer, the term of this patent is extended or adjusted under 35 U.S.C. 154(b) by 18 days.

(21) Appl. No.: 13/003,011

(22) PCT Filed: Jun. 25, 2009

(86) PCT No.: PCT/EP2009/057960
§ 371 (c)(1),
(2), (4) Date: Jan. 7, 2011

(87) PCT Pub. No.: WO2010/003829
PCT Pub. Date: Jan. 14, 2010

(65) Prior Publication Data
US 2011/0125094 A1 May 26, 2011

(30) Foreign Application Priority Data
Jul. 8, 2008 (EP) .................................... 08159931

(51) Int. Cl.
*A61M 5/00* (2006.01)
(52) U.S. Cl.
USPC ........................................................ 604/110
(58) Field of Classification Search
USPC ........................................................ 604/110
See application file for complete search history.

(56) References Cited

U.S. PATENT DOCUMENTS

| 4,737,144 A | 4/1988 | Choksi | |
|---|---|---|---|
| 4,738,663 A | 4/1988 | Bogan | |
| 4,927,416 A | 5/1990 | Tomkiel | |
| 5,219,338 A * | 6/1993 | Haworth | 604/198 |
| 5,795,336 A * | 8/1998 | Romano et al. | 604/192 |
| 7,611,491 B2 * | 11/2009 | Pickhard | 604/139 |
| 2004/0127857 A1 * | 7/2004 | Shemesh et al. | 604/198 |
| 2006/0200077 A1 * | 9/2006 | Righi et al. | 604/110 |
| 2007/0129674 A1 * | 6/2007 | Liversidge | 604/110 |
| 2011/0125094 A1 * | 5/2011 | Weist | 604/110 |

FOREIGN PATENT DOCUMENTS
FR    2613628    10/1988

* cited by examiner

*Primary Examiner* — Nicholas Lucchesi
*Assistant Examiner* — Diva K Chander
(74) *Attorney, Agent, or Firm* — Husky Intellectual Property Services

(57) ABSTRACT

The invention relates to a cannula protector that serves to cover a cannula which has been attached to a syringe, particularly for the purpose of preventing unintended damage to the cannula as well as contamination of the cannula shortly before its use on the patient. The invention also relates to a single-use syringe system with such a cannula protector.
A cannula protector according to these principles includes a tubular sleeve and a bellows which, in part together with the sleeve, completely encloses at least the area of the cannula. The cannula protector usually also comprises a radially acting clamp or engagement spring, whose function is to hold the inserted single-use syringe in the desired position, or to activate the protective mechanism.

14 Claims, 3 Drawing Sheets

CANNULA PROTECTOR AND SINGLE-USE SYRINGE SYSTEM

BACKGROUND

Various needle protection devices are known from the state of the art. The brief storage of single-use syringes that have been prepared for the injection, until the time of the performance of the injection, as well as the disposal of already used single-use syringes, is of particular importance because of the risk of infection with various pathogens, and because of the risk of damage to the exposed cannula.

From DE 100 44 383 C2 a needle protection device is known, which is used on a cannula which can be attached to a single-use syringe. The needle protection device comprises a carrier and a needle sleeve. The needle sleeve can be moved out of a retracted position into a protection position in which it envelopes the puncture needle at least up to the needle tip. The needle sleeve comprises a bellows, and locking elements which form a locking telescope that assumes a locking position in the deployed state. The needle protection device relates exclusively to the cannula which, after the use of a single-use syringe, can again be removed from the latter.

From EP 0 763 369 B1, a needle protection device with collapsing sleeve is known. The needle protection relates to a catheter where, as a collapsing sleeve, a bellows which can be moved against a spring force is used. The sleeve reliably and automatically protects the sharp tip of the introduction needle of the catheter, after the needle has been used for placing a catheter on a patient. The protection device has a complicated structure with many individual parts, and a complicated spring engagement mechanism for the activation of the protection mechanism. The bellows is formed from a flexible, impermeable, nonelastic material with low expansion properties. The individual parts of the protection sleeve are assembled in an elaborate way, for example, by press fitting, ultrasound welding, or the use of a standard glue.

From US 2004/0127857, a multipart cannula protector with an outer sleeve and an inner protection sleeve is known. Between the internal and external sleeves, elaborate mechanical means are provided in order to mutually fix the sleeves, for the purpose of the injection, and "countersink" the needle within the outer sleeve for the manual or automatic release of a resetting mechanism. In an embodiment, inside the inner sleeve, a spiral spring is integrally formed with the sleeve.

From U.S. Pat. Nos. 4,927,416 and 5,795,336 A, syringes with multipart needle protection covers are known, which act against a spring tension.

U.S. Pat. No. 4,738,663 A describes a lengthwise divided needle protection device which, for mounting on a syringe, presents a snap connection with a nose and groove.

In U.S. Pat. No. 4,737,144 A, a needle protection device to be moved onto a syringe is disclosed, which can be fixed by means of radial engagement elements or bayonet closure.

From FR 2 613 628 A, a single-use syringe is known. A closing mechanism with engagements and a predetermined breaking edge on the syringe plunger are intended to make it impossible to reuse the syringe.

SUMMARY

The invention is based on the problem of providing a cannula protector for the reliable covering of a cannula attached to a syringe, which cannula protector can be manufactured in large quantities in a particularly simple and cost effective way. The cannula protector should be designed preferably as a one-time use protecting sleeve and may be suitable for use on single-use syringes. To optimize the protection of used syringe parts against infection, a system with a cannula protector is also to be provided, which prevents the reuse of not only the cannula but also the single-use syringe.

The problem is solved by a cannula protector according to the attached claim 1, and by a single-use syringe system according to claim 12.

The cannula protector according to the invention presents a tubular sleeve for axially moveable accommodation of a syringe, preferably a single-use syringe. The tubular sleeve is closed at one of its ends by a base, where the base has an opening for the passage of a cannula attached to the single-use syringe. At the other end of the sleeve, a compressible spring element is constructed as a bellows, and is formed as a single piece, where the bellows presents a preliminary tension, so that it resumes its original shape after compression in the axial direction and subsequent release.

The sleeve and the bellows have dimensions in terms of total length such that the single-use syringe with attached cannula is completely enclosed by the cannula protector over its entire axial extent at least in the area of the cannula. The bellows must overall be capable of being compressed by approximately the length of the cannula, so that the cannula, when the single-use syringe is inserted for the purpose of the injection, can move substantially entirely out of the opening. Advantageously, the cannula protector is made available in various sizes and, in each case, with bellows of different lengths.

The sleeve length is shorter than the length of the syringe cylinder of the syringe to be inserted. The compression length is at least equal to the length of the cannula of the syringe to be inserted. The sum of the sleeve length and stretched length of the bellows is at least equal to the sum of the length of the syringe cylinder and the length of the cannula.

In the case of an axially directed pressure on the bellows, the single-use syringe is moved in the cannula protector, which results in the cannula being released through the opening in the base.

The cannula protector comprises, moreover, at least one radially acting clamp spring which is arranged in the area of the sleeve. Preferably several clamp springs are provided with uniform distribution over the periphery of the sleeve.

The clamp spring or the clamp springs can be actuated by the finger pressure of two fingers that grip the sleeve, in order to press the clamp spring(s) against the inserted single-use syringe, and to keep the latter in the instantaneous position. This is done for the purpose of injection, when the cannula extends out of the opening.

According to the invention, the bellows is under pressure, that is, when the syringe is moved with the cannula in the direction of the opening, the bellows can be pressed together, and as a result of spring elasticity it resumes its original shape after the release, namely when the clamp springs are released, particularly when the syringe is put down.

The advantages of the invention are particularly that the cannula protector can be manufactured in a particularly simple and cost effective way, for example, by an injection molding method. The cannula protector according to the invention can be used in connection with conventional syringes, without the need to have to change the design of the latter.

In a preferred embodiment of the invention, the bellows is in the shape of a screw. The latter can be manufactured preferably by the injection molding method using a rotating core which, after the casting, is twisted out of the finished cannula protector. In this way, the cannula protector can be removed easily from the mold, without having to be sectioned into several parts. Consequently, the entire cannula protector can be formed as a single part.

Advantageously, two clamp springs are arranged radially opposite each other, or four clamp springs are arranged with uniform distribution over the periphery. However, it is equally possible to select a different number of clamp springs. The clamp springs are preferably designed so they constitute a single piece with the sleeve, by forming tongue-shaped clamp springs which, to facilitate the actuation, present a section that protrudes beyond the wall of the sleeve. The—in each case radially opposite—positions of two clamp springs promote the actuation of the clamp mechanisms when the syringe is gripped with two fingers by the operator.

It is preferred that a scale of the inserted single-use syringe can be observed, in spite of the enclosing cannula protector. This can be achieved advantageously by one or more axially running slits in the sleeve. However, it is also possible to manufacture the cannula protector completely or in sections from a transparent plastic material.

The cannula protector can be designed as a single piece, or, in an advantageous embodiment, it can be divided into two in the axial direction, in such a way that it can be assembled by means of an engagement mechanism.

The opening for the passage of the cannula has preferably a circular shape, but other shapes, such as, for example, the shape of a cross, are also possible.

A particularly advantageous single-use syringe system comprises a cannula protector of the above-described type and a single-use syringe, where the single-use syringe or part thereof can be locked undetachably by means of a connection notch with the cannula protector. The single-use syringe system according to the invention prevents a new use of the single-use syringe inserted into the cannula protector.

In a preferred embodiment of the single-use syringe system, the plunger of the single-use syringe is provided with a predetermined breaking edge to prevent reuse, and, in the interior of the syringe cylinder, a flange which is narrowed in cross section close to the outlet is provided, which destroys the predetermined breaking edge as the latter strikes the flange, so that the plunger after use is no longer mounted with seal in the single-use syringe.

In a second preferred embodiment of the single-use syringe system, a closing mechanism is provided on an actuation system of the single-use syringe and on the cannula protector, which mechanism, after a one-time closing actuation of the syringe plunger, engages, and as a result prevents, a repeated use of the single-use syringe.

BRIEF DESCRIPTION OF THE FIGURES

Preferred embodiments of the invention are explained in further detail below in reference to the figures.

DETAILED DESCRIPTION

Figure 1:
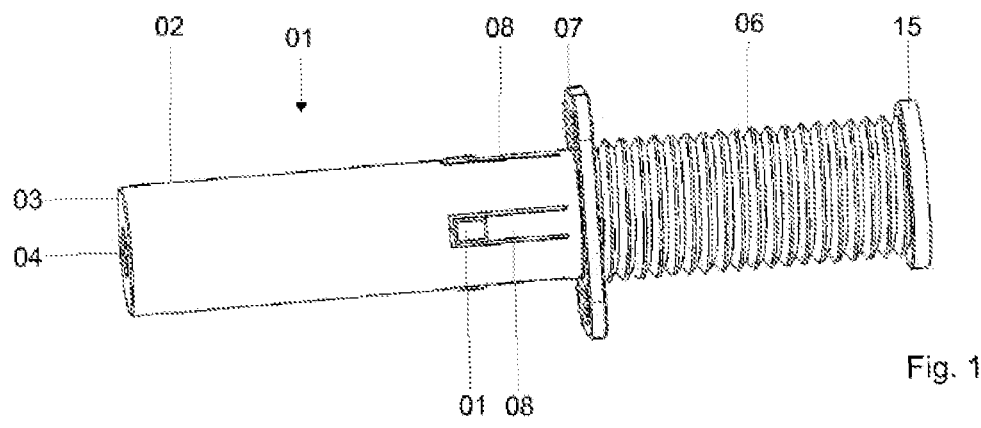
FIG. 1 is a spatial view of a cannula protector.
Figure 2:
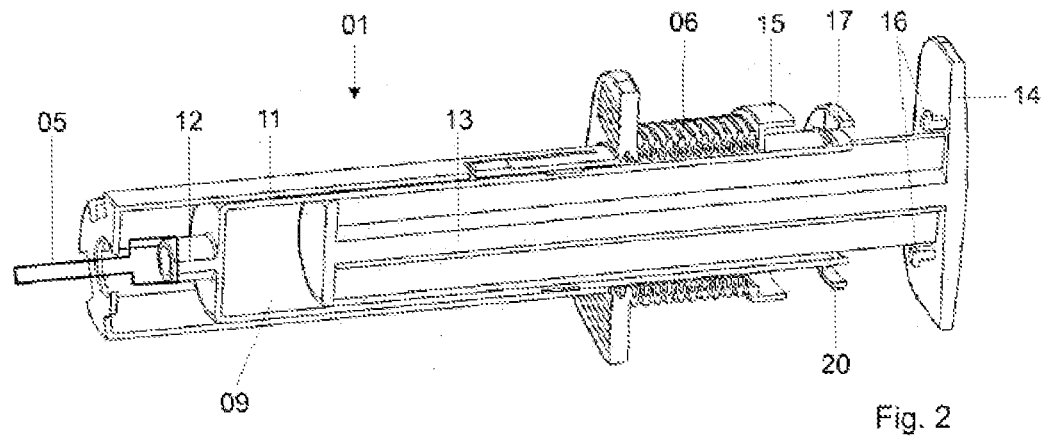
FIG. 2 is a longitudinal cross-sectional representation of the cannula protector with inserted single-use syringe.

FIG. 1 shows a cannula protector 01 in a spatial representation. The cannula protector 01 comprises a tubular sleeve 02. The sleeve 02 is closed at its first end by a base 03, which presents an opening 04 for the passage of a cannula 05 (FIG. 2) of a single-use syringe 09 (FIG. 2). The represented opening 04 has a circular shape. However, it is also possible to use other suitable shapes, such as, for example, a cross or the like.

A bellows 06 forms a single piece with an end of the sleeve 02, which faces the base 03. The bellows 06 is under a preliminary tension, and it can be pushed together or compressed under pressure in the axial direction. When the pressure is released, the bellows 06 resumes its original shape. The bellows 06 is preferably formed with a coiled wall, so that it works like a helical spring. The bellows 06 is represented here in the completely stretched state. The resetting force to be applied by the bellows in the compressed state must be sufficiently large so that the sleeve 02 is moved axially forward on the syringe and receives the cannula, as soon as no force is applied by the user to the entire system. At the same time, the counterforce of the bellows to be overcome during the injection should be as small as possible, so as not to make the injection more difficult.

Between the sleeve 02 and the bellows 06, two projecting parts 07 are preferably arranged, which function to allow the holding of the cannula protector 01 with two fingers, when the single-use syringe is inserted into the cannula protector, or during the injection.

On the periphery of the sleeve 02, in the represented embodiment, four radially-acting clamp springs 08 are arranged, which, when pressure is oriented radially on them, hold the inserted single-use syringe in the instantaneous position in the sleeve 02, preferably with the cannula uncovered for the injection.

The arrangement of four clamp springs 08 distributed over the periphery has been found to be advantageous, because, as a result, the cannula protector 01 does not have to be rotated with inserted single-use syringe, to operate the clamp springs with two springs. The usual one-hand operation of the syringe also continues to be possible with the cannula protector 01.

The clamp springs 08 are formed as springy tongues forming one piece with the sleeve 02, and they have a radial overhang 10 for easier actuation.

FIG. 2 shows a longitudinal cross-sectional representation of the cannula protector 01 according to the invention, with a single-use syringe 09 inserted in it. The single-use syringe 09 comprises, in a known way, a syringe cylinder 11 with a nozzle 12 for the attachment of the cannula 05. The single-use syringe 09 comprises, moreover, a syringe plunger 13 with an actuation plate 14 for pushing the syringe plunger 13 into the syringe cylinder 11.

The entire single-use syringe 09 can be moved axially together with the attached cannula 05 inside the cannula protector 01, and, by pressing the clamp elements 08, it can be fixed in the given position. The sleeve 02 presents, between the base plate 03 and the projecting part 07, at the other end, a sleeve length which is shorter than the length of the syringe plunger 11. The bellows 06 is represented in the largely-compressed position, which can only be maintained if the user actuates the clamp elements 08, and thus clamps the syringe in the sleeve 02. In a representation which is different from the one chosen in FIG. 2 to facilitate the understanding, the free end 15 of the bellows 06 abuts, during the actuation of the syringe, against a stop ring 20 of the syringe plunger 11, so that the bellows is compressed when a force is exerted in the axial direction on the syringe plunger or the actuation plate 14 of the syringe plunger. The friction between the syringe cylinder 11 and the internal wall of the sleeve 02 is kept sufficiently small by providing enough clearance, so that the syringe can be moved substantially only against the resistance of the bellows into the sleeve 02.

The compression length of the bellows 06, by which the latter must be compressed at least, and by which it has to expand again after the removal of the compression force, corresponds at least to the length of the cannula 05 (possibly minus its foundation), to achieve a complete covering of the cannula during the expansion of the bellows and the associated movement of the sleeve 02.

Before the injection proper, the user uncovers the cannula 05 by pushing the syringe into the sleeve 02. The injection can then be positioned as usual. If the user puts down the syringe out of his/her hand, the clamping force disappears, the bellows 06 undergoes a release of tension, and in the process moves the sleeve 02 over the cannula 05.

The syringe plunger 13, in the state represented in FIG. 2, is moved far into the syringe cylinder 11. This corresponds to the time during the injection or when the injection solution is sucked into the syringe.

In the embodiment represented in FIG. 2, the cannula protector 01, together with the single-use syringe 09, forms an advantageous single-use syringe system, which is fitted with the cannula 05, and which can also be delivered in this completed form, filled with an injection solution.

The actuation plate 14 of the syringe plunger 13 presents, for the purpose of mechanical locking after use, two radially opposite engagement hooks 16, which, after complete insertion of the syringe plunger 13 into the syringe cylinder 11, engage in an engagement groove 17. In the represented embodiment, the engagement groove 17 is arranged on the syringe cylinder 11 of the single-injection syringe 09; however, in a specially preferred embodiment, the engagement groove 17 can be arranged directly at the end of the bellows 06, resulting in an advantageous undetachable connection between the single-use syringe 09 and the cannula protector 01 after use of the single-use syringe 09. The function of the cannula protector is not affected by the engagement of the engagement hooks, so that, after completion of the injection, a locking of the single-use syringe as well as a covering of the used cannula is obtained.

Figure 3:
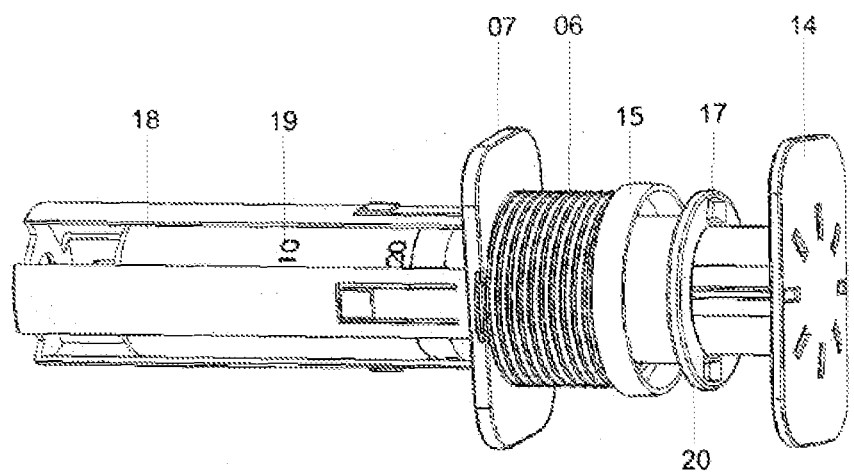
FIG. 3 is a spatial view of a second embodiment of the cannula protector.

FIG. 3 shows a spatial representation of the single-use syringe system according to FIG. 2. The cannula protector 01 presents axially running viewing slits 18, preferably four distributed over the periphery, which allow the observation of a scale 19 of the single-use syringe 09. The observation possibility is also necessary to be able, for example, to observe the flow of blood into the syringe.

Figure 4:
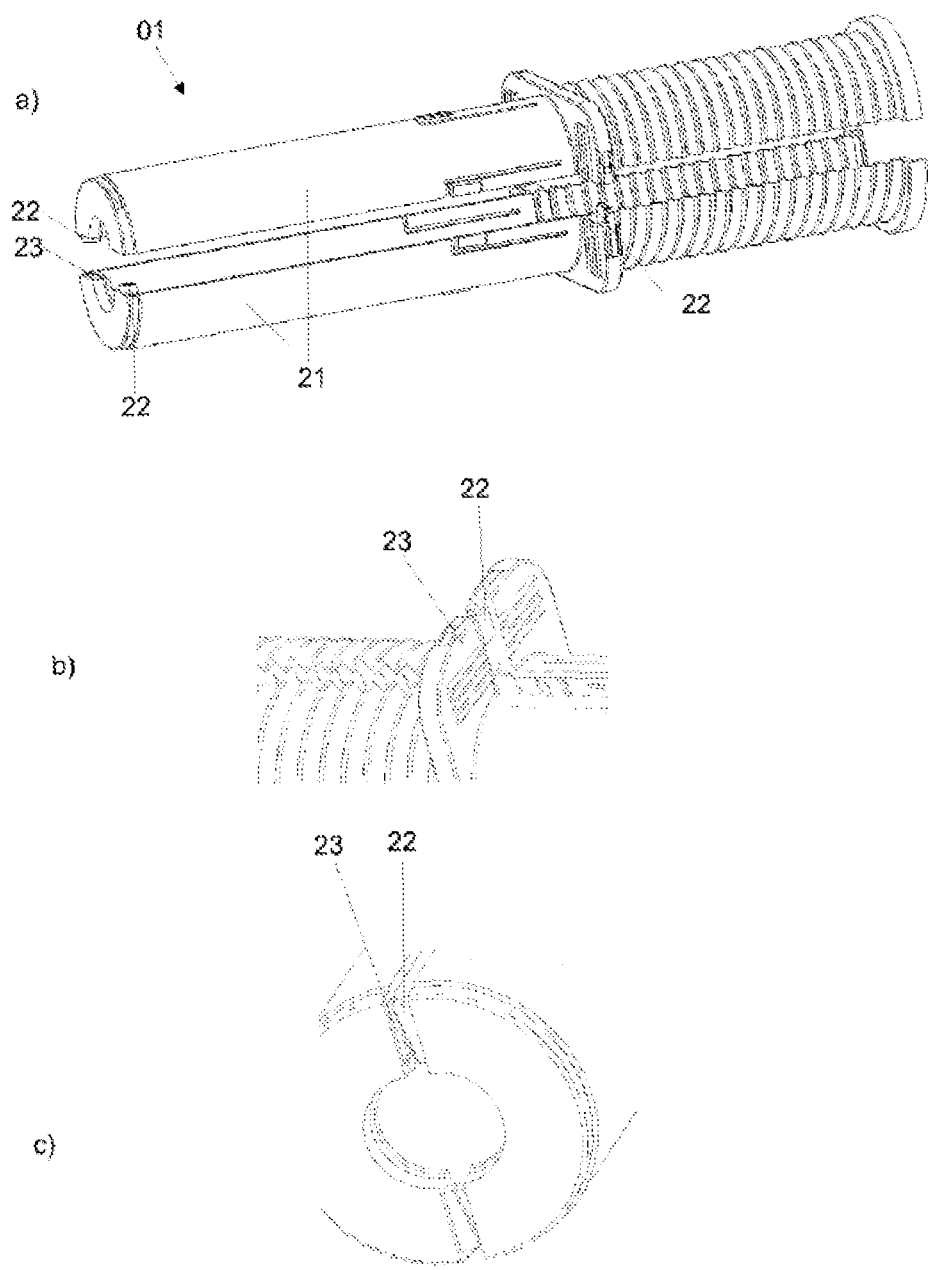
FIG. 4 are three spatial detail representations of a cannula protector in a two-part design.

FIG. 4 shows, in three views, the cannula protector 01 which is divided into two in the axial direction, and which can be assembled from two halves 21. This embodiment is particularly cost-effective in its manufacture, because the injection molds can have a substantially simpler design. In the two-part design, the bellows 06 can have a shape without a coiled structure.

In Figures b) and c), the engagement mechanism for connecting the halves 21 is represented in detail. The two halves 21 present preferably each a nose 22 and a groove 23 at three axially distributed connection places.

A completely prepared respectively-filled single-injection syringe can be inserted advantageously into one of the halves, and encapsulated by snapping the second half shut. As a result, the handling is simplified. There are no special requirements in terms of the sealing properties of the cannula protector 01, and therefore the two-part embodiment can be used preferably.

Figure 5:
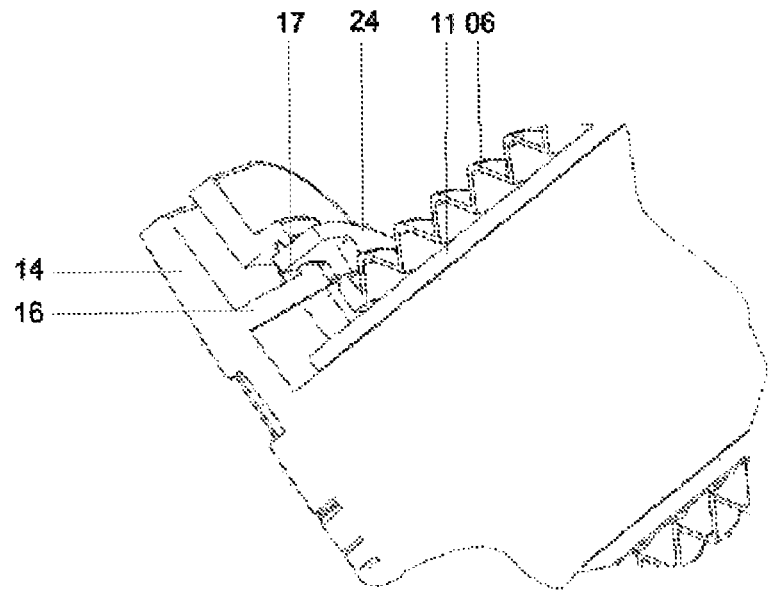
FIG. 5 is a detail view of a closing mechanism of a single-use syringe system.

FIG. 5 shows a detail view of an engagement mechanism of a single-use syringe system similar to the one already described in FIG. 2. In addition to the already-described function, the bellows 06 presents a fixation section 24 which engages during assembly in the engagement groove 17 provided in the syringe cylinder 11 of the single-use syringe 09. The engagement hook 16 of the syringe plunger 13, after completion of the actuation, also engages in this engagement groove 17, which reliably prevents repeated opening or use of the single-use syringe.

Figure 6:
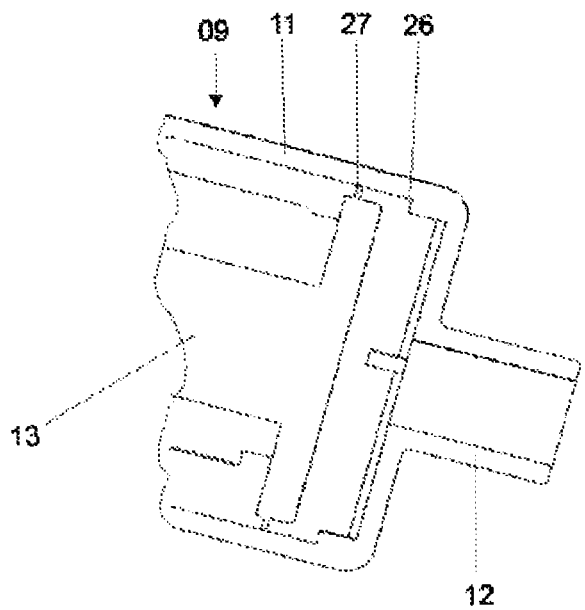
FIG. 6 is a detail view of a single-use syringe.

FIG. 6 shows a detail view of a preferred embodiment of a single-use syringe 09 to be used in the single-use syringe system. The syringe cylinder 11 presents, in its interior, close to the outlet which is provided with the nozzle 12, a flange 26 which strikes a predetermined breaking edge 27, which is provided on the syringe plunger 13 and which is narrowed in cross section, during the closing actuation of the single-use syringe 09, destroying it in the process. As a result of the destruction of the predetermined breaking edge 27, the syringe plunger 13 is no longer mounted with seal in the syringe cylinder 11, and thus it is no longer possible to suck an injection solution again into the single-use syringe.

The combination of the described characteristics leads to a single-use syringe system which satisfies stringent hygiene requirements. The risk of damage to the cannula is minimized, because the cannula is protected by the cannula protector, as soon as the syringe is no longer held by the hand. At the same time, reuse is prevented.

The invention claimed is:

1. A combination of a cannula protector for covering a cannula attached to a syringe and the syringe, the combination comprising: a single tubular sleeve for axially moveable accommodation of the syringe having a syringe cylinder with a base at one of its ends, the base having an opening for the passage of a cannula; a spring element formed on another end of the sleeve, the spring element which, by application of a compression force against an elastic resetting force that is intrinsic to the spring element, can be compressed axially by a predetermined compression length, and which automatically resets when the compression force is removed, wherein a free end of the spring element abuts against a stop ring of the syringe cylinder of the syringe, when it is moved into the sleeve, in order to move the cannula outwards through the opening; wherein the spring element is a bellows, and wherein at least one radially acting clamp spring is arranged on the sleeve, in order to push, as a result of a radially applied force, against the syringe which is moveable in the sleeve, and to clamp it, and wherein the cannula protector is divided into two in the axial direction and the cannula protector can be assembled by means of an engagement mechanism, after the syringe has been inserted.

2. The combination according to claim 1, wherein the sleeve length of the sleeve is shorter than the length of the syringe cylinder of the syringe, the compression length is at least equal to the length of the cannula, and the sum of the sleeve length and the stretched length of the bellows is at least equal to the sum of the length of the syringe cylinder and the length of the cannula.

3. The combination according to claim 2, wherein the cannula protector is designed as a single piece.

4. The combination according to claim 1, wherein the bellows is in the shape of a screw.

5. The combination according to claim 1, further comprising four clamp springs arranged in radially opposite pairs on the sleeve.

6. The combination according to claim 1, wherein the sleeve has an axially running slit to expose the syringe, particularly a scale, to view.

7. The combination according to claim 1, wherein the cannula protector is manufactured from plastic.

8. The combination according to claim 1, wherein the cannula protector is manufactured by injection molding.

9. The combination according to claim 1, wherein the opening is in the shape of a circle or in the shape of a cross.

10. The combination according to claim 1, wherein the cannula protector presents an engagement groove for retentive accommodation of a single-use syringe.

11. A combination according to claim 1, wherein the syringe is a single-use syringe, wherein the single-use syringe comprises a syringe cylinder with a nozzle for the attachment of a cannula, and a syringe plunger with an actuation plate, and wherein the syringe cylinder can be locked by means of a connecting notch with the cannula protector.

12. The combination according to claim 11, wherein the syringe plunger is provided with a predetermined breaking edge, and, in the interior of the syringe cylinder, close to the outlet, a bar is provided, which is configured to destroy the predetermined breaking edge as it strikes, so that the syringe plunger is subsequently no longer mounted with seal in the syringe cylinder.

13. The combination according to claim 11, wherein, on the actuation plate of the syringe plunger, and on a stop ring of the syringe cylinder, a closing mechanism is provided, which, after the one-time complete introduction of the syringe plunger into the syringe cylinder, prevents the syringe plunger from being pulled out again.

14. The combination according to claim 11, wherein, on the actuation plate of the syringe plunger and on the cannula protector, a closing mechanism is provided, which, after the one-time complete introduction of the syringe plunger into the syringe cylinder, prevents the removal of the syringe from the cannula protector.

* * * * *